United States Patent
Keenan et al.

[11] Patent Number: 5,447,692
[45] Date of Patent: Sep. 5, 1995

[54] ON-LINE PROCESS FLOW AND REACTION MONITOR

[75] Inventors: Charles A. Keenan, Irvine; Peter J. Coassin, San Juan Capistrano; David B. Helphrey, Santa Ana; Roger Winer, Playa Del Rey; Jiunn-Jye Dih, Yorba Linda, all of Calif.

[73] Assignee: Beckman Instruments, Inc., Fullerton, Calif.

[21] Appl. No.: 337,311

[22] Filed: Nov. 10, 1994

Related U.S. Application Data

[63] Continuation of Ser. No. 936,976, Aug. 28, 1992, abandoned, which is a continuation-in-part of Ser. No. 909,231, Jul. 6, 1992, abandoned.

[51] Int. Cl.[6] .............. G05B 17/00; G01N 21/00; G01F 1/708; G01F 13/00
[52] U.S. Cl. ................... 422/116; 422/62; 422/81; 422/82.05; 422/110; 436/43; 436/164; 436/165; 73/861; 73/861.05; 73/861.41
[58] Field of Search ............. 422/62, 63, 81, 82.05, 422/107, 108, 110, 114, 115, 116; 435/287, 291, 808; 436/43, 164, 165; 935/77, 85, 88; 204/82.8; 73/861, 861.05, 861.41

[56] References Cited

U.S. PATENT DOCUMENTS

| | | | |
|---|---|---|---|
| 3,557,077 | 1/1971 | Brunfeldt et al. | 935/88 |
| 4,668,476 | 5/1987 | Bridgnam et al. | 422/62 |
| 4,816,695 | 3/1989 | Lavin | 356/436 |
| 5,047,524 | 9/1991 | Andrus et al. | 536/27 |
| 5,073,345 | 12/1991 | Scott et al. | 356/436 |
| 5,096,671 | 3/1992 | Kane et al. | 422/82.07 |
| 5,106,585 | 4/1992 | Minami et al. | 422/116 |
| 5,112,134 | 5/1992 | Chow et al. | 356/436 |
| 5,150,174 | 9/1992 | Ryczek et al. | 356/402 |
| 5,171,534 | 12/1992 | Smith et al. | 422/116 |

FOREIGN PATENT DOCUMENTS

| | | |
|---|---|---|
| 60-069095 | 4/1985 | Japan . |
| 60-072898 | 4/1985 | Japan . |
| 60-228498 | 11/1985 | Japan . |
| 1-058340 | 6/1989 | Japan . |
| WO90/11291 | 4/1990 | WIPO . |

OTHER PUBLICATIONS

Kellenbach, "Geautomatiseerde Peptidesynthese", Chemisch Magzine, Aug. 1989. pp. 450 & 452.

Primary Examiner—Robert J. Warden
Assistant Examiner—Christopher Y. Kim
Attorney, Agent, or Firm—William H. May; P. R. Harder; Schneck & McHugh

[57] ABSTRACT

The present invention makes use of a single detector to monitor several process functions, e.g. reaction efficiency, reagent flow rates, the presence of empty reagent reservoirs, the absence of a chemical reactor column in the system, blockage of flow system, etc., at a single location in the flow system. In accordance with the detection scheme of the present invention, only one detector is required to accomplish the same, if not more, functions as many detectors in the prior art instruments. In the described embodiment, an optical detector is positioned downstream of a chemical reaction chamber. This detector monitors the effluent from the reaction chamber to monitor the reaction efficiency. It also monitors the system functions upstream of the reaction chamber. System flow rate is monitored by detecting the presence of a gas bubble which has been introduced into the system at a known instance. Depletion of reagents in the reservoirs can be detected by monitoring the absence of the reagents at the detector at times when the reagents are expected. The flow system may be periodically diagnosed to check for flow blockage or missing flow component, by monitoring the flow past the detector which corresponds to a predetermined succession of reagents introduced into the system. Any deviation from a predictable succession of changes in the flow monitored by the detector indicates possible blockage of the flow delivery system or missing flow components.

17 Claims, 9 Drawing Sheets

TRITYL DETECTOR SIGNAL AS A FUNCTION OF TIME DURING DEBLOCKING STEP

FIG. 9C

ON-LINE PROCESS FLOW AND REACTION MONITOR

This is a continuation of application Ser. No. 07/936,976 filed on Aug. 28, 1992, now abandoned, which is a Continuation-in-Part application of U.S. patent application Ser. No. 07/909,231, filed on Jul. 6, 1992, now abandoned.

BACKGROUND OF THE INVENTION

1. Field of the Invention

The present invention relates to automated chemical processes, and more particularly, to monitoring of process efficiency as affected by reagent flow and reaction.

2. Description of Related Art

Automated chemical processors for processes such as DNA (nucleic acid) synthesis, peptide synthesis and peptide sequencing generally require a system of valves and interconnecting tubings to deliver a predetermined series of chemicals to a reactor in which a desired series of chemical reactions takes place. The chemistries of these processes are well known. DNA synthesis, for example, is described generally in U.S. Pat. No. 4,458,066 issued to Caruthers et al, entitled "Process for Preparing Polynucleotides", which is incorporated by reference herein. This process involves the linking of nucleotides, which are the basic building blocks for DNA, to construct a single-stranded oligonucleotide. One of several approaches in synthesizing DNA is the so-called solid-phase phosphoramidite method which generally involves the steps of deblocking, activation, coupling, capping and oxidation in each synthesis cycle to add a nucleotide to a strand anchored to a solid-phase support. In an automated DNA synthesis apparatus, typically a delivery system dispenses a number of chemical reagents in predetermined sequence in a cycle into a reaction column according to instructions from the system controller or computer. After the desired number of cycles are completed, the operator removes the reaction column from the automated system and performs additional chemical procedures to retrieve the synthesized DNA fragment from the reaction column. In executing the automated steps, a variety of undesirable conditions may arise which lead to reduced efficiency or premature termination of the desired chemical reactions. For example, one undesirable condition is deterioration of one or more sensitive chemicals such that they no longer react efficiently. Other conditions include partial blockage of delivery tubing such that the desired chemical reagents are delivered at a reduced rate, and the depletion of chemical reagent in a particular reagent reservoir.

It is desirable to detect the above-mentioned conditions when they occur and to stop the process so that the conditions may be corrected before proceeding further. In the past, operators of automated DNA synthesis apparatus have engaged in the practice of observing the effluent from the chemical reactor to ascertain that the reaction is proceeding efficiently and that all the desired chemicals are flowing properly. Reaction efficiency is typically judged by observing the intensity of a characteristic bright orange color in the effluent containing dimethoxytrityl ion at a particular step of the process known as the deblocking step. Flow rates are often judged by measuring the volume of effluent over a fixed interval of time. However, the requirement for an operator to monitor constantly the operation of an automated instrument defeats much of the objective of automation. Attempts have been made in the past to monitor the flow system. For example, Biosearch Corporation has employed optical detectors on the delivery tubes from individual reagent reservoirs to detect the absence of reagents in the tubes. Pharmacia Instruments/LKB has provided in its commercial DNA synthesizer an on-line colorimeter to monitor dimethoxytrityl ions effluent and to derive therefrom a measure of reaction efficiency. This instrument automatically shuts down if reaction efficiency falls below a predetermined threshold. For all these instruments, a separate detector is required for each monitoring function, which adds to the complexity and cost of the instrument.

SUMMARY OF THE INVENTION

The present invention makes use of a single detector to monitor several process functions, e.g. reaction efficiency, reagent flow rates, the presence of empty reagent reservoirs, the absence of a chemical reactor column in the system, blockage of flow system, etc., at a single location in the flow system. In accordance with the detection scheme of the present invention, only one detector is required to accomplish the same, if not more, functions as many detectors in the prior art instruments.

In the described embodiment, an optical detector is positioned downstream of a chemical reaction chamber. This detector monitors the effluent from the reaction chamber to monitor the reaction efficiency. It also monitors the system functions upstream of the reaction chamber. System flow rate is monitored by detecting the presence of a chemical discontinuity or liquid-gas interface (i.e. meniscus) which has been introduced into the flow stream at a known time. Depletion of reagents in the reservoirs can be detected by monitoring the absence of the reagents at the detector at times when the reagents are expected. The flow system may be periodically diagnosed to check for flow blockage or missing flow components, by monitoring the flow past the detector which corresponds to a predetermined succession of reagents introduced into the system. Any deviation from a predictable succession of changes in the flow monitored by the detector indicates possible blockage of the flow delivery system, depleted reagents or flow components missing.

DESCRIPTION OF THE ILLUSTRATED EMBODIMENT

The following description is of the best contemplated mode of carrying out the invention. This description is made for the purpose of illustrating the general principles of the invention and should not be taken in a limiting sense. The scope of the invention is best determined by reference to the appended claims.

While the present invention is described in the context of DNA synthesis, it is to be understood that the present invention can be implemented for other types of chemical reaction processes.

DNA SYNTHESIS SYSTEM CONFIGURATION

The Flow System

Figure 1:
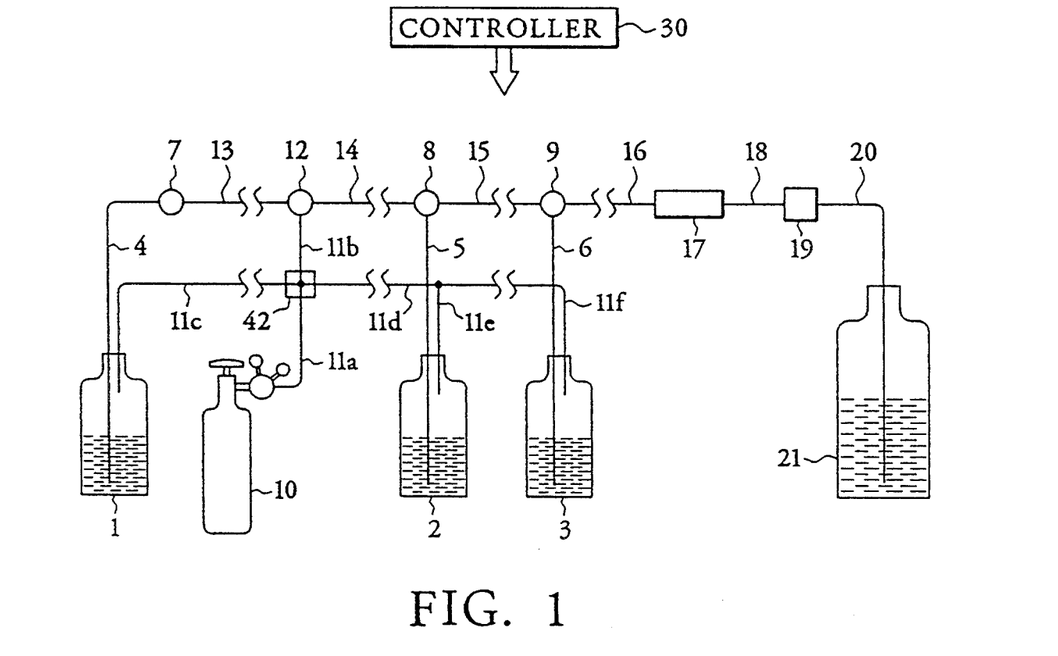
FIG. 1 is a simplified schematic arrangement of an automated chemical processing apparatus in accordance with one embodiment of the present invention.
Figure 2:
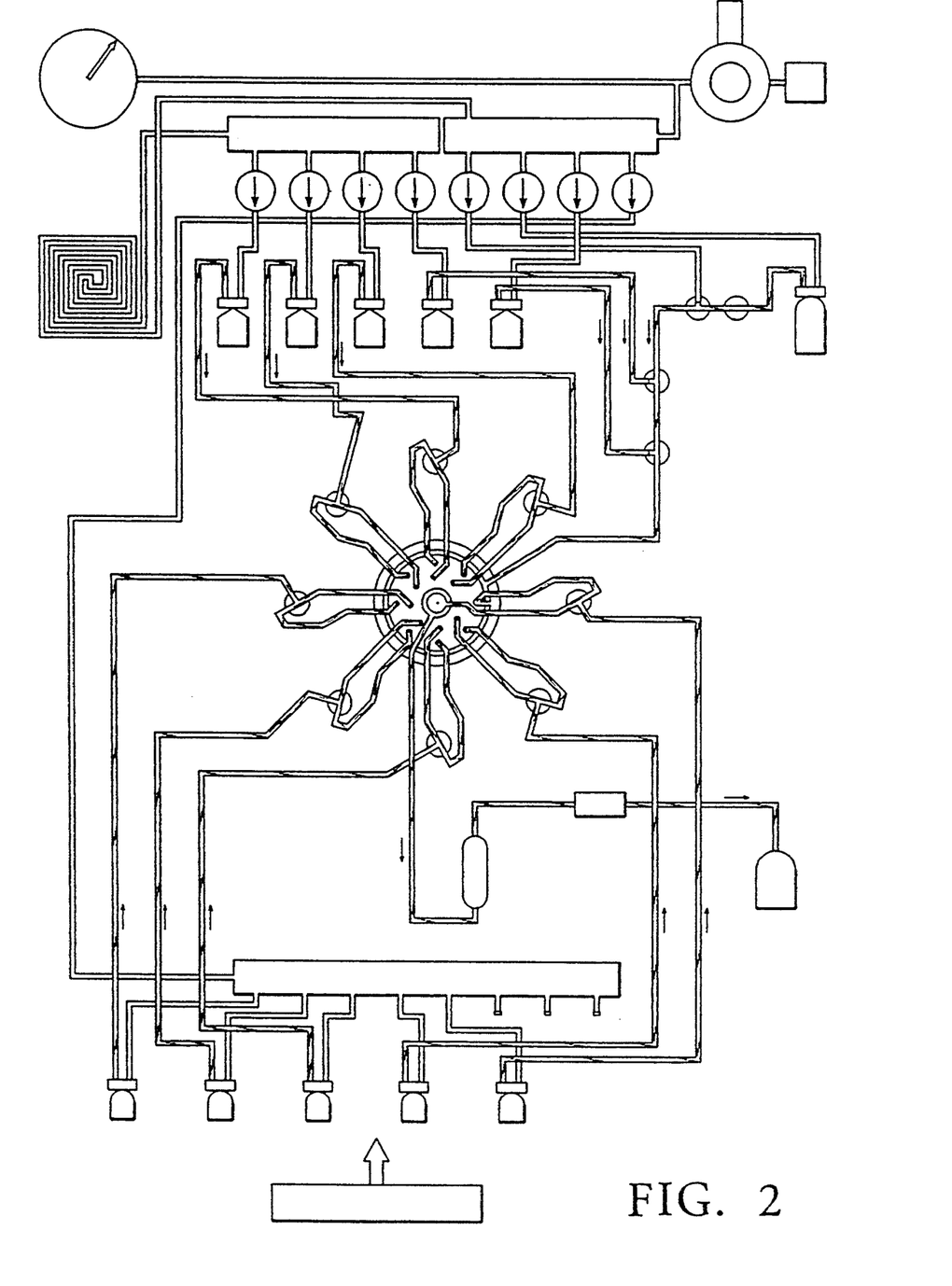
FIG. 2 is an elaborate schematic flow diagram of an automated DNA synthesizer in accordance with one embodiment of the present invention.

FIG. 1 illustrates the simplified schematic arrangement of an automated chemical processing apparatus suitable for use to synthesize DNA. This is a simplified fluid diagram for the purpose of illustrating the basic concept of the invention. A fully automated apparatus typically comprises more reagent reservoirs and additional flow components. It is within the knowledge of one skilled in the art to incorporate the necessary reagent reservoirs and flow components to build an automated DNA synthesizing apparatus which incorporates the present invention in light of the disclosure of U.S. Pat. No. 4,458,066 to Caruthers et al which is incorporated by reference herein. A more detailed flow schematic is shown in FIG. 2 which will be explained in greater detail below.

Referring to FIG. 1, reservoirs 1, 2 and 3 contain appropriate chemical reagents for DNA synthesis. Tubings 4, 5 and 6 have ends immersed in the reagents and are connected to valves 7, 8 and 9 which turn on and off fluid delivery from the reservoirs 1, 2 and 3. The valve 7 is a normally-closed two port valve. When it is actuated, it permits flow from tube 4 to tube 13. When it is released, it blocks flow between tubes 4 and 13. The valves 8 and 9 are normally-closed 3-port 2-way valves. When one of these valves is actuated, all its ports are opened, so that flow may occur in any direction through any port. When the valve is released, only the port connected to the associated reservoir is closed. The valves 7, 8 and 9 may be of the electromechanical type which are actuated under control by controller 30. While the valves are shown to be connected in series, a rotary valve 40 may be implemented to form similar or additional valving functions as illustrated in FIG. 2.

Each reservoir 1, 2 and 3 is capped. Tubes 11a, c–f deliver a pressurized (at substantially constant pressure ~4–5 psi) inert gas such as helium from a tank 10 to above the reagent level in each reservoir. Consequently, when a valve (7, 8, 9) is actuated, the reagent in the reservoir connected to that valve is forced into the associated supply tube (4, 5, 6) and through the valve by the pressurized gas. If system pressure drops below an acceptable level, the controller 30 pauses the synthesis process to prompt the user to rectify the source of the problem. A manifold (42) is provided to distribute the pressurized gas to the reservoirs. An additional valve 12 connected to the pressurized gas tank 10 is provided at a point in the fluid system which is downstream from valve 7. When this valve is actuated, gas is injected into the flow stream to interrupt the continuity of the chemical reagent flow. Downstream of the valves is a chemical reaction chamber 17 in which the desired chemical reactions take place, in this case synthesis of oligonucleotides. Further downstream is a detector 19 positioned along or adjacent the flow path 18 to monitor the passing fluid flow. At the very end of the flow system 20, a waste container 21 is provided to collect the spent reagents that have flowed through the system, or a collection device (not shown) is provided if so desired to collect selected byproducts from the chemical reactions.

An actual DNA synthesizing apparatus consists of many more reservoirs and valves than depicted in FIG. 1, but its operation may be adequately described with reference to this simplified fluid system for the purposes of discussing the current invention.

In operation, the reagents in the reservoirs are delivered to the reaction chamber by actuating one or more of the valves 7, 8, 9 in a desired sequence for the particular chemical reactions desired to take place at the reaction chamber 17. For example, the valve 7 is actuated to permit the reagent from the reservoir 1 to flow through the tubes 4, 13, 14, 15 and 16 and reaction chamber 17 followed by actuation of the valve 8 to permit the reagent from the reservoir 2 to flow through the tubes 5, 15 and 16 and enter reaction chamber 17. A mixture of the reagents may be delivered by actuating two or more of the valves simultaneously. The synchronization of valve actuations as well as other system functions described herein are controlled by a programmable controller 30.

Figure 2A:
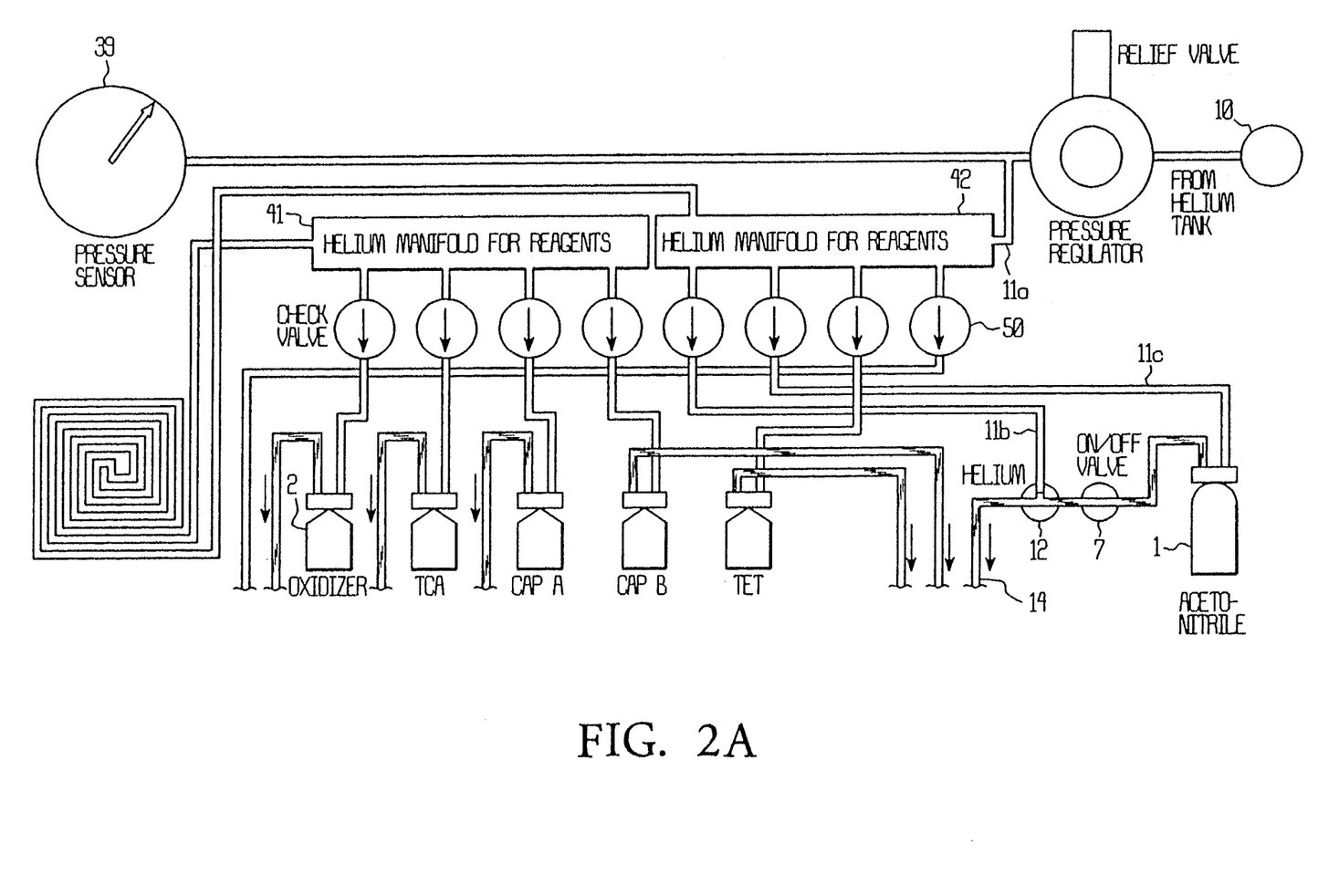
FIG. 2A is a partial view of reagent manifolds shown in FIG. 2.
Figure 2B:
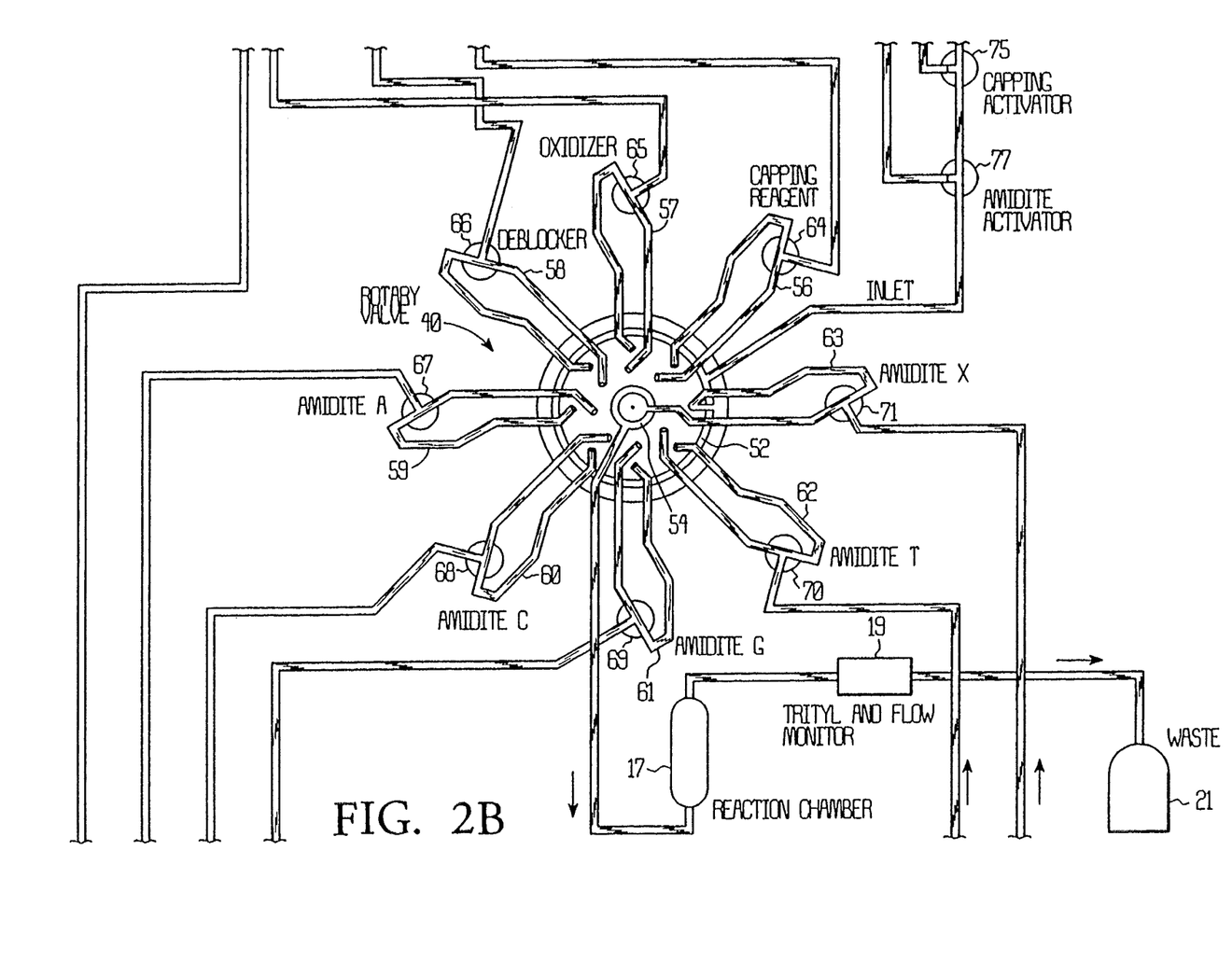
FIG. 2B is a partial view of a rotary valve shown in FIG. 2.
Figure 2C:
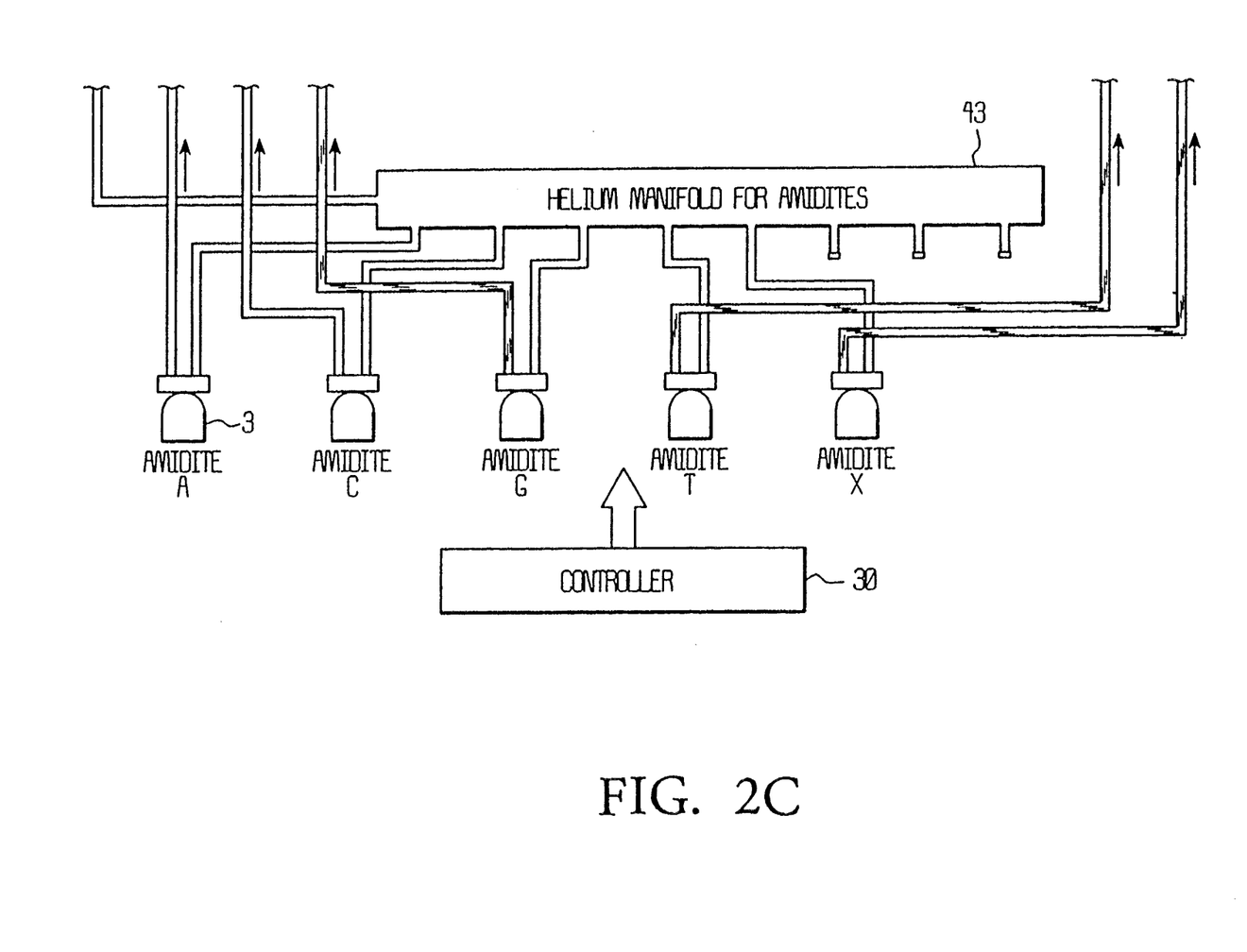
FIG. 2C is a partial view of a manifold for amidites shown in FIG. 2.
Figure 2D:
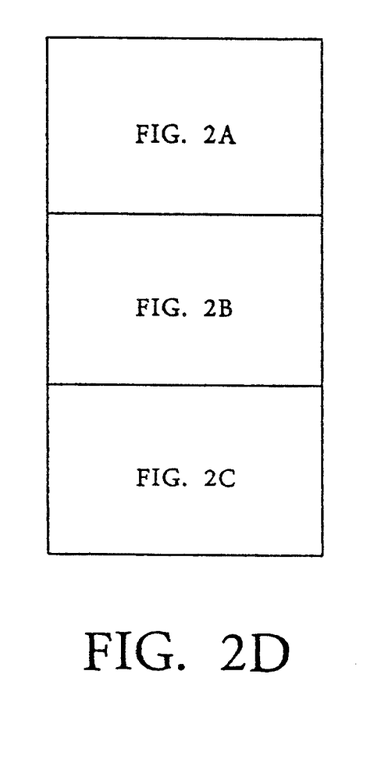
FIG. 2D is a construction view demonstrating the appropriate alignment of FIG. 2A, FIG. 2B, and FIG. 2C of the DNA synthesizer shown in FIG. 2.

Referring to FIG. 2, a more elaborated schematic diagram of an automated DNA synthesizing instrument is set forth. Similar parts as in the schematic of FIG. 1 have been labeled with the same reference numbers. In this schematic, manifolds are clearly shown for distribution of the pressurized helium gas. Specifically, referring to FIGS. 2A–2C there are three manifolds 41, 42 and 43 having their plenums interconnected. On two of the manifolds 41 and 42, checkvalves 50 have been provided at the plenum outlets to prevent back flow of reagent vapors from the reservoirs (1, 2, etc.) which contain liquid reagents. All the essential chemical reagents for DNA synthesis are identified on the diagram. As shown in the diagram, capping activator 74 and amidite activator 76 are injected into the acetonitrile flow stream through individual valves 75 and 77 along the input flow path 14 to the rotary valve 40. In the "heart" of the instrument is a multi-port rotary valve 40 which directs delivery of the various chemical reagents to the reaction column 17. The rotary valve 40 is the subject matter of a copending U.S. patent application (Ser. No. 07/909,232 filed on Jul. 6, 1992 and commonly assigned to the assignee of the present invention) and therefore this will not be explained in every detail. It is sufficed to understand that the rotary valve 40 has an annular input 52 for the solvent acetonitrile, an annular output 54 to the reaction column 17, and several branches 56 to 63 between the annular input 52 and output 54 at which selected chemical reagents are selectively injected into the branches through control of additional individual valves 64 to 71. A more detailed discussion of this system is found in the copending patent application. The rotary valve 40 is rotated under control by the controller 30 to access the different branches 56 to 63 in a predetermined sequence to deliver chemical reagents in accordance with known DNA synthesis process such as that disclosed in the Caruthers patent which has been incorporated by reference herein. By the use of the individual valves 64 to 71 in combination with the rotary valve 40, cross-contamination of the chemical reagents can be reduced. Moreover, the distances traveled by the various chemical reagents injected into the branches 64 to 71 of the rotary valve 40 to the reaction column are the same which makes the control of the synchronization of the valves 56 to 63 more easily implemented. The illustrated system is suitable for use with reaction chambers 17 that are designed for synthesis of 30, 200 and 1000 nmole oligonucleotides. Other sizes may be used with appropriate modification of flow components with respect to their capacities.

Detector/Monitor

Figure 4:
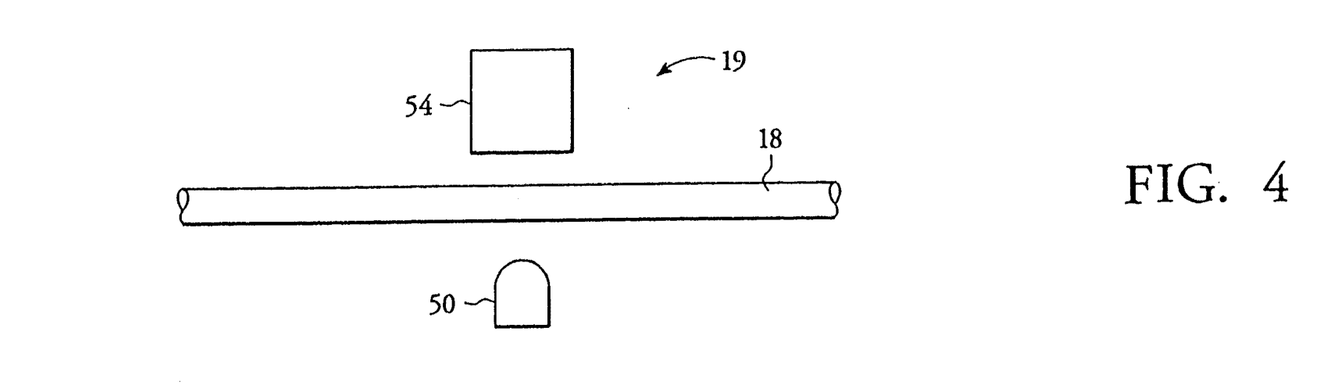
FIG. 4 is a schematic configuration of an optical detector including a blue LED.
Figure 5:
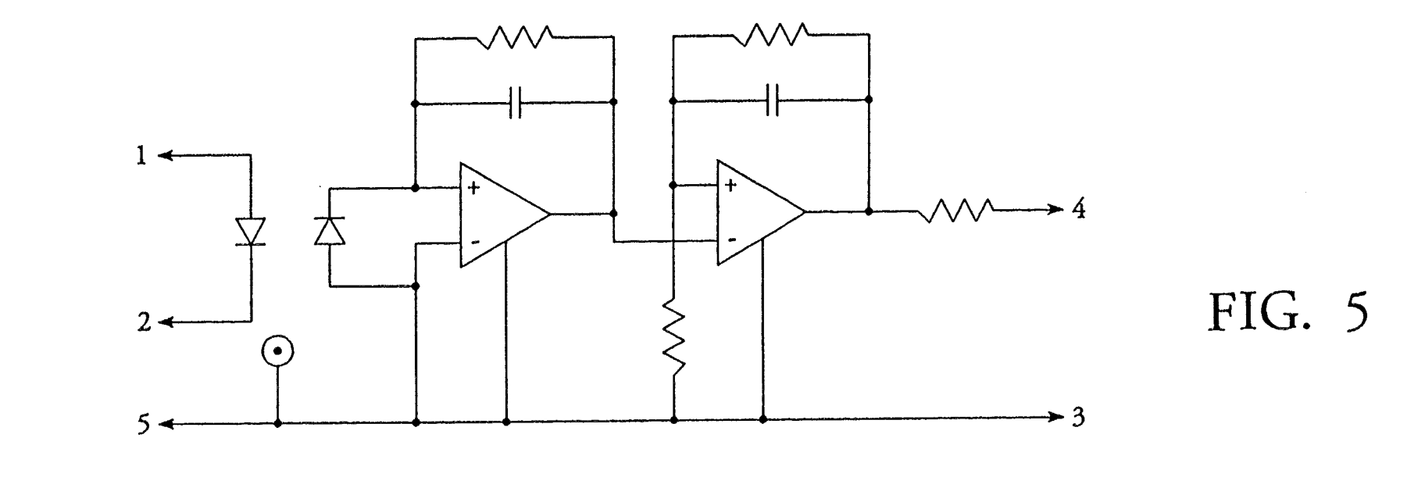
FIG. 5 is a circuit diagram for the LED detector.

The detector 19 can be of the type that detects changes in optical or electrical conductive characteristics of the reagents passing through the tube 18. Preferably, an optical detector is used in the system. This includes a light source and light sensitive detecting element. In the case of DNA synthesis, the optical detector should be able to sense the intensity of the bright orange-colored dimethoxytrityl ion (DMT) byproduct of the deblocking step flowing from the reaction chamber 17. In other instances, the optical detector should be able to distinguish between the reagents from the reservoirs by sensing differences in absorbance or refractive index in the flow stream. Furthermore, the optical detector should be able to detect the presence of a gas bubble in the reagent stream. A preferred optical detector includes a silicon carbide blue light emitting diode (LED) and a silicon photodiode photosensitive element. The configuration of the detector is schematically shown in FIG. 4. The light from the blue LED 50 is focused through the tube 18 and transmitted light is detected by photodiode 54. The tube 18 should be transparent to the LED light. Preferably, FEP (Fluorinated Ethylene Polypropylene) tubing is used since it is inert to the chemicals in the system and is relatively transparent to LED light. FIG. 5 shows the circuit diagram for the detector. The blue LED may be obtained from Cree Research, Inc. in Durham, N.C., U.S.A. and the silicon photodiode may be obtained from Hamamatsu Corp. in Japan. The detector 19 generates a voltage signal proportional to the blue LED light level detected by the photodiode 54. Each reagent attenuates the light and reduces the signal level by a characteristic amount, so the signal provides a means of identifying which fluid is present at the detector. The signal generated by the detector is communicated to the controller 30 through an analog-to-digital converter ("ADC") (not shown) fifty times per second during the synthesis process. The driving current for the LED is adjusted so that the ADC counts for all measurements are within full range. The detector readings are employed for a variety of functions as described below.

SYSTEM MONITORING FUNCTIONS

The system is implemented with several monitoring functions to ensure the integrity of the synthesis products (oligonucleotides) and efficiency of the synthesis process. It is necessary to monitor system performance as well as conditions of the system components to assure that they have not significantly changed before and during synthesis. The following sections describe the various monitoring functions. This is followed by descriptions of the system calibration functions and algorithm methodologies for carrying out the various system functions.

Trityl Monitoring

Figure 3:
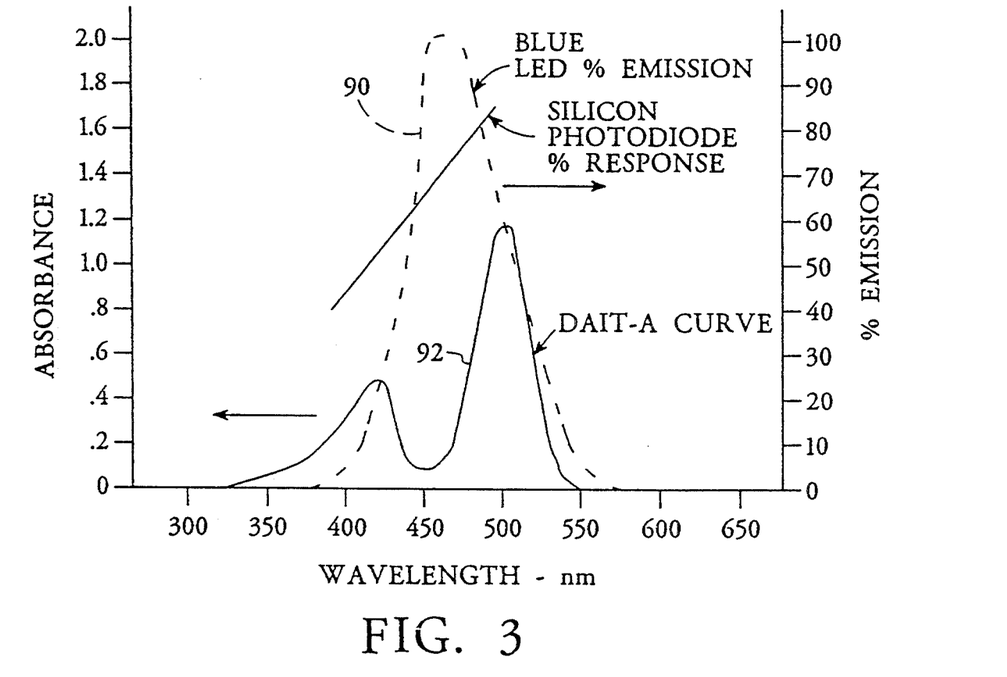
FIG. 3 is a graph showing the emission characteristic of the blue LED and absorbance characteristic of DMT solution.

The blue LED has a spectral characteristic 90 as shown in FIG. 3, which also shows the relative absorbance characteristic 92 of the DMT product. The DMT product absorbs light primarily of wavelength from 350 to 550 nm. Blue LED emits light primarily of wavelength from approximately 400 to 550 nm, with peak emission at about 470 nm. Consequently, the blue LED is an efficient source of light for detection of DMT product. Ultraviolet light source would not be suitable as most of the light in the ultraviolet range is not absorbed by the DMT. The absorbance depends upon the concentration of DMT. Hence the absorbance signal can be employed to estimate the quantity of DMT released by the deblocking step which provides an indication of the reaction efficiency leading to the desired end product, which in this case is synthesized oligonucleotide. If reaction efficiency were for some reason reduced, DMT byproduct would be less.

Figure 6:
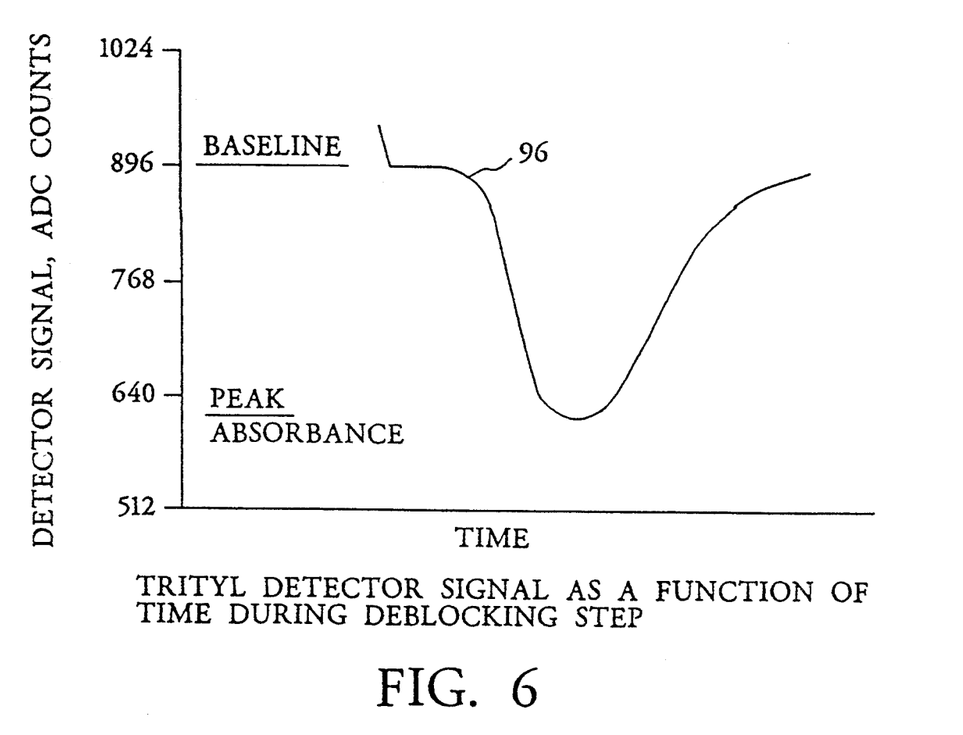
FIG. 6 is a graph of detector signal as a function of time, during a deblocking step of DNA synthesis.

The detector signal is measured as a function of time during the course of the deblocking step to estimate the quantity of DMT present. FIG. 6 shows an idealized profile 96 of a detector signal (in ADC counts) which relates to transmittance (inverse to absorbance) during a deblocking step. From the profile, the instrument measures the difference in signal level between the base line and the minimum which occurs where DMT absorbance is maximum (peak absorbance). From this value the relative quantity of DMT released may be determined by comparison to a known reference. The quantity of released DMT is referred to as the DMT yield of the cycle.

Synthesis Coupling Efficiency

The coupling yield of a given synthesis cycle is assumed to be equal to the DMT yield of the following deblocking reaction times a correction factor for each amidite. This is expressed by the equation:

$$Y_i = T_i \times A_i \tag{1}$$

where
$Y_i$ = coupling yield on cycle i
$T_i$ = DMT yield on cycle i+1
$A_i$ = nucleoside correction factor for the nucleoside at cycle i The nucleoside correction factors compensate for the fact that trityl yields for G nucleosides are systematically higher than average, and yields for A, C and T nucleosides are lower than average. The correction factors $A_i$ can be determined empirically from experimental studies. The following correction factors for A, C, G and T nucleosides have been experimentally obtained for the system described herein. These factors may vary depending on other system parameters.

$A_A = 1.00$
$A_C = 1.00$
$A_G = 0.85$ (for 30 nmole synthesis)
$A_G = 0.94$ (for 200 nmole synthesis)
$A_T = 1.00$ Using these correction factors and the observed DMT yields, the instrument calculates the coupling yields $Y_i$ according to equation (1). Then it applies the following tests to evaluate whether coupling efficiency is acceptable:

Test 1:

For cycle 1, is the coupling yield less than 80 ADC counts? (The normal first cycle yield is about 300 ADC counts for a 30 nmole column and 550 ADC counts for a 200 nmole column.) This test is designed to detect whether something is drastically wrong with the column, the deblocking reagent or the synthesis system.

Test 2:

For cycle 2, is $Y_i$ less than 30% of $Y_0$? This test is designed to detect catastrophically poor coupling efficiency on the first cycle. It may indicate wet phosphoramidite or activator reagents or poor delivery of phosphoramidite/activator mixture to the column.

Test 3:

For cycles 2 through 15, is the coupling yield less than 80 ADC counts on two successive cycles? This test detects failure less catastrophic than Tests 1 and 2, but nevertheless very severe. It will detect a sharp drop in efficiency in a synthesis which had been going well up to the last two cycles.

Test 4:

For cycles 3 through 40, is the yield on cycle i less than 85% of the yield on cycle $i-1$ for two successive cycles? In other words, is $(Y_i/Y_{i-1}) < 85\%$, and is $(Y_{i-1}/Y_{i-2}) < 85\%$? This test is similar to Test 3, but detects less severe failure and is applied for more of the synthesis.

Tests 5 and 6 are applied on cycles 4 through 40 and differ between the 30 nmole and 200 nmole scales:

Test 5:

For 30 nmoles, is the yield on cycle i less than 80% of the yield on cycle $i-1$, and is the average coupling efficiency for steps 1 through i less than 90%? For 200 nmoles, is the yield on cycle i less than 80% of the yield on cycle $i-1$, and is the average coupling efficiency for steps 1 through i less than 96%?

Average coupling efficiency is given by $$E = 10 \exp [(\log Y_i - \log Y_1)/(i-1)] \quad (2)$$

Test 6:

For 30 nmoles, is the average coupling efficiency calculated on three successive cycles less than 91%? For 200 nmoles, is the average coupling efficiency calculated on three successive cycles less than 96%?

Failure to exceed any of the above six tests causes the synthesizer to pause synthesis. Failure of an efficiency test is ordinarily fatal to a synthesis. Nevertheless, the synthesis system is programmed to provide the user with the options of aborting synthesis or continuing in spite of the failure.

Helium Detection

Because the walls of the tubing are highly curved, the detector signal is also strongly affected by index of refraction of the passing stream. In particular, the low refractive index of helium has the effect of deflecting most light rays so that very little signal at all is transmitted through the tubing and detected when helium passes by the detector 19. Consequently, helium appears to be comparatively opaque. The detected signal for helium is substantially lower than for any reagent except oxidizer. The signal level for oxidizer is distinguishably lower than for helium.

Flow Rate Monitoring

To monitor flow rates at a given nominal flow pressure, the length of time required for a reagent to flow between two points in the flow system is measured. This may be simply accomplished by detecting a transition between the signal characteristic of the reagent and the signal characteristic of helium, i.e. detecting the liquid gas interface. One approach is that a helium gas bubble is emitted to the flowing stream by activating the valve 12 momentarily at a known time. The time required for this bubble to reach the detector 19 is indicative of the flow rate of the reagent stream in which the gas bubble is entrained.

A preferred approach for flow rate monitoring is to measure the time taken for a reagent to flow in a purged flow path. In this approach, helium valve is first opened for a sufficient length of time to purge all liquids from tubings 14-16, 18 and 20 and reactor 17. After the entire flow path has been helium purged to the waste container 21, the valve 7 is opened to allow acetonitrile to fill the path to the detector 19. The arrival of acetonitrile at the detector is detected by the change from the optical characteristic of helium to the optical characteristic of acetonitrile. The length of time from the opening of the valve 7 until detection indicates the rate of flow in the section of flow path upstream from the detector 19. If there is abnormality in the flow delivery system upstream of the detector 19, such as blockage of flow or absence of certain flow components (e.g. the reactor column), the actual elapsed time for the flow will deviate from the expected time. If flow rate is below acceptable level, system pauses for user to rectify the source of the problem.

To detect flow obstructions downstream from the detector 19, after the preceding step, the flow path from the detector 19 to the waste container 21 is filled with acetonitrile. Then valve 7 is closed and valve 12 is opened to allow helium to fill the path from the valve 12 to the detector 19. The arrival of helium at the detector is detected by the transition to the 'helium' signal level.

The system may be programmed to perform flow rate tests during system startup and periodically (e.g. during each cycle of or between synthesis runs) or on demand by the user. The system may be programmed to monitor flow rate through all eight flow paths through the rotary valve 40 (associated with valve branches 56-63). For each flow path, the test is applied four times, and if all four measurements agree sufficiently, the average for each valve is compared with empirically established standards to determine whether flow rates are acceptable. The measured flow rate is stored for use in memory for use in conjunction with the other flow monitoring functions in the system. Furthermore, all reagent bottle may be filled with acetonitrile and flow is measured as delivered from each reagent bottle through the respective reagent control valves (64-71) and flow paths.

Reagent Depletion Monitoring

The detector 19 can also be used to indicate whether reagent in one of the reservoirs has been depleted. If a bottle empties, then the pressurizing helium gas passes through the bottle and into the flow path through the reagent control valve for that reagent. Appearance of helium at the detector when reagent is supposed to be present indicates that the reagent bottle must have emptied and helium gas is being delivered from its head space.

Figure 7:
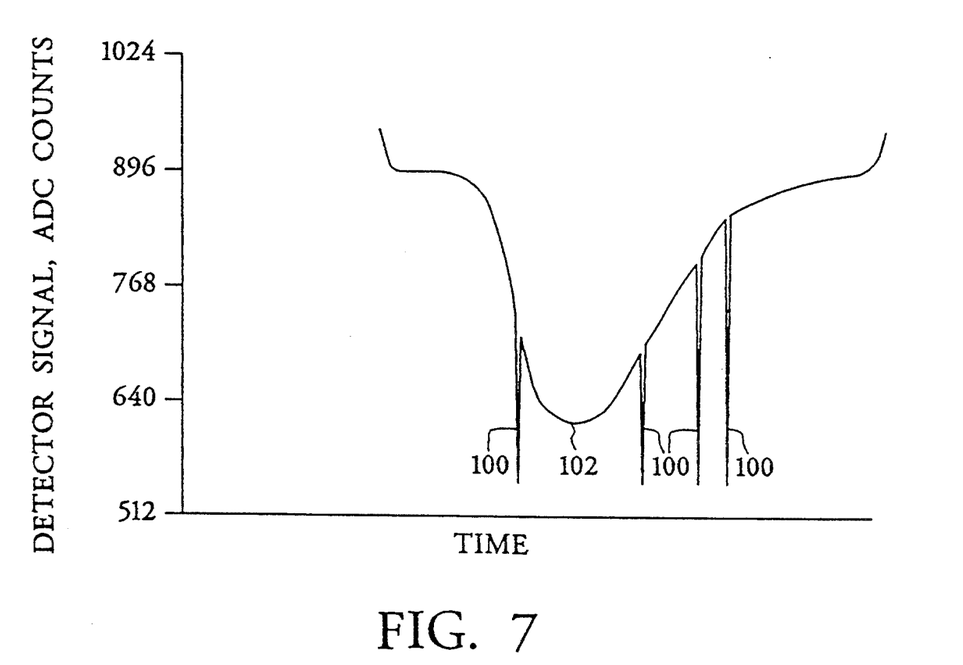
FIG. 7 is a graph of detector signal showing the characteristics of helium bubble entrained in the flow.

It is noted that the use of helium to purge reagents and the injection of helium to the solvent stream for washing causes tiny bubbles to be lodged in the reactor column. As reagents flow through the column, these bubbles tend to dislodge at random times and become entrained in the flow past the detector. Referring to FIG. 7, because of low transmittance of the helium bubbles, they appear in the detector signal as instantaneous "peaks" 100 of low detector signal. These peaks must not be mistaken for genuine transitions to helium flow, and must not be mistaken for high absorbance of DMT during the deblocking step. The narrow helium peaks 100 are discriminated from the broad, slow changing peak 102 associated with DMT ion absorbance by their short duration (see discussion on signal filtering below). When a large number of helium peaks 100 are observed during a step when reagent should be flowing past the detector, it is an indication that helium is being injected in the flow path in large quantities. The usual circumstance for this condition to occur is when one of the two reagents being delivered in a mixture of two reagents has emptied.

An alternate approach may be utilized for detecting reagent depletion which is more suitable for situations in which two reagents are delivered at the same time. During solvent wash after reagent delivery has been completed, the flow path is filled with solvent. The reagent control valve of the 'suspected' empty bottle is opened to deliver a bolus of reagent into the flow path leading to the detector 19. Solvent is then continued to be delivered to push the bolus until the bolus has passed detector 19. If helium bubble is observed at about the time that reagent bolus was anticipated, it is probable cause to believe that originating bottle is empty. If probable cause is established, the preceding three steps are repeated as many times as required to establish certainty. If bottle is empty, the system pauses synthesis to allow user to rectify problem, i.e. replenish bottle. The system resumes thereafter to complete synthesis. To conserve reagent, this approach might be applied only in two circumstances: 1.) as a confirmatory test when the previously described algorithm detects a 'suspected' empty bottle. 2.) on amidite and capping reagents when the recorded use of these reagents predicts that a bottle is nearly empty.

The system may be programmed such that after each refill of reagents, it estimates reagent usage for the particular synthesis run and warns user of low reagent level before start of synthesis to avoid interruption during synthesis. Further the system may be programmed to automatically confirm estimated empty bottle condition (described below).

Gas Pressure Monitor

The pressure monitor employs a sensor 39 (FIG. 2) to detect pressure in the helium pressurization system. The instrument examines the output of this sensor at the start of every cycle of a synthesis and before performing a solvent wash or prime. When the sensor output moves any farther than 20% above or below an established set point, the instrument pauses synthesis and flushes the system with acetonitrile. The sensor set point is calibrated and set to the pressure level which yields a certain average steady-state flow rate (e.g. 10.0 ml/min for 30 to 1000 nmole synthesis scale) for acetonitrile through each of the eight system flow paths associated with the rotary valve 40.

SYSTEM CALIBRATION

In order for the system monitoring functions to be effectively carried out, it is necessary to calibrate the detector signal with respect to the reagent absorbance characteristics. The following sections are directed to provisions for checking system conditions and calibrating conditions of various system components.

Leak Test

Prior to the initial run of the system, the system should be checked for leaks. The system is tested for helium leaks. Helium is introduced into empty reagent bottles which are positioned in their respective places in the system and having their associated valves closed. The helium pressure in the system is detected using the pressure sensor 39 (FIG. 2A) and a drop in pressure over a period of time (e.g. 1.0 psig in 2 minutes) signifies leaks in the system.

The system is also tested for liquid leaks. Acetonitrile is placed into bottles in place of reagents and the system is run with the acetonitrile introduced into the system flow paths. Liquid leaks in the system can be visually determined and appropriate corrective action is taken.

Missing Reaction Column Detection

If the reaction column 19 is missing, the detector can detect this condition. The system is programmed to do an initial purge during system start-up or at the beginning of each synthesis followed by washing with acetonitrile. Therefore, the first signals expected at the detector should be a "helium" signal within an expected time period after the beginning of helium introduction and an acetonitrile signal following thereafter. If the reactor column is missing, due to oversight of the laboratory operator, the helium characteristic signal would not be initially detected indicating that a flow component is probably missing.

Flow Rate Calibration

The standards for the flow rates along the flow paths in the system can be initially determined in accordance with the procedures outlined in the "Flow Rate Monitoring" section above. The same test can be performed at any time typically between synthesis runs to automatically establish a new calibration of the reagent offset table.

Detector Calibration

The output voltage of each detector is somewhat different from other detectors, owing to differences in LED brightness, photodiode sensitivity and detector optics. Furthermore, a given detector's output changes over time as the components age or as the tubing darkens. For these reasons the detector 19 must be calibrated periodically and its output adjusted so that it spans the optimum range of the analog-to-digital converter (ADC).

For the purpose of identifying which fluid is present at the detector at any time, the instrument requires a table of detector signal levels characteristic of the various reagents and of helium, obtained by measuring the detector signal for each of these fluids during system installation. If the characteristic signal levels change over time, the system may begin to give spurious indications of empty bottles, poor flow rates, low trityl yields or other error conditions. In this event, it is necessary to reestablish calibration.

Calibration of the detector 19 is carried out by filling the detector with acetonitrile solvent (lowest transmittance signal), measuring the ADC output and adjusting LED drive current until the ADC output achieves the desired level. Helium and the reagents (except phosphoramidites which are relatively expensive and transmittances of which are close to acetonitrile) are then delivered to the detector 19 to establish calibration values as well as set the lower and upper ends of the ADC count range by adjusting the drive current to the LED. This calibration is carried out automatically when the system is installed. Thereafter, detector output is monitored at the beginning of every synthesis to verify that it has not changed significantly. The system may be programmed such that when detector output changes enough to require recalibration, the system displays a message to the user to prompt performing a detector calibration. If calibration fails, the test is repeated.

The relative signal characteristics (in inverted digital counts, or 1023 minus ADC counts) of helium and the different reagents are as follows:

| | |
|---|---|
| Oxidizer | 760–880 |
| Helium | 550–700 |
| Capping; Deblock | 170–250 |
| Acetonitrile; Amidites; Amidite activator | 65–130 |

Preferably, the relative signals of the reagents should be at least 15–20% different from that of helium in order for the monitor function to adequately distinguish helium from the reagents in the flow stream based on the detector data.

SYSTEM 'CONDITIONING'

Discussed below are means for 'conditioning' the flow system for improving synthesis efficiency and effectiveness of system monitoring functions with respect to calibrated values.

Reagent Prime

Priming of reagent supply tube is required in two circumstances, either: 1) the reagent bottle has been replaced and an air bubble has been introduced into the tube while the bottle was off; or 2) the reagent contained in the supply tube has been standing for such a long period of time that it may have deteriorated because of exposure to contaminants which have diffused through the wall of the tube. In either case, the remedy is to deliver a sufficient quantity of reagent to replace the contents of the supply tube with fresh reagent from the bottle.

The system is programmed to check immediately before delivering any reagent to see whether priming is required. If its bottle has been replaced (user interrupted the system and indicated to the system that a bottle has been replaced) or if the reagent has been standing for too long a period of time since the last time it was delivered, then the synthesizer automatically primes the affected reagent supply tube. After the tube has been primed, the system proceeds with normal delivery of the reagent.

Solvent Wash and Helium Purge

For each step of the synthesis cycle to proceed efficiently, the reagent delivered should be as pure as possible. It must not be contaminated by chemicals from preceding steps. The most striking example of this is the coupling step, where water contamination from the oxidation step of the preceding cycle could seriously degrade coupling efficiency. To insure purity of the reagents delivered, each step in a synthesis cycle is both preceded and followed by a washing process including helium purge. Typically, acetonitrile solvent is placed in reservoir 1 and is used to wash residue chemicals from the valves, the tubing and the reactor column 17 before initiating subsequent steps.

Preferably, the solvent wash step is performed with injected segments of helium gas to break up laminar flow effects which otherwise seriously impede the effectiveness of washing the tubings and valves with solvent. During solvent wash a film of reagent tends to cling to the walls of the flow system so that large volumes of solvent are required to wash the reagent away completely. A suitable means to combat these effects is to inject segments of helium gas into the solvent stream. Turbulence at each interface between solvent and gas scours the tubing walls and dramatically increases the washing efficiency. A segmented stream of acetonitrile in reservoir 1 is delivered by opening the valves 7 and 12 in rapid alternation while valves 8 and 9 are closed. The solvent with entrained helium bubbles passes through the tubings (14, 15, 16, 18, 20), valves (8,9), reaction column 17 and the detector 19 to the waste container 21.

Also for efficient reaction, the reagent delivered in each step must be as concentrated as possible, undiluted by solvent. To minimize dilution of reagents, the wash solvent from the tubing and reactor column 17 should be purged with helium gas immediately prior to the delivery of each reagent. After helium purge, it is desirable to fill the flow path from the helium control valve 12 to just before the affected reagent control valve (64–71) with acetonitrile solvent before delivering reagent so as to leave only a small segment of helium between the acetonitrile stream and the reagent introduced through the valve (a "solvent block" step). This is necessary to prevent delayed reagent delivery to the reaction column 17 caused by compression of large helium gas segments upstream of the reagent control valve.

Helium purge is also employed to minimize the use of solvent for washing. When a reaction is complete, the old reagent is purged with helium before starting solvent wash. This reduces the quantity of reagent which must be rinsed out with solvent, and thereby reduces the volume of solvent required for thorough cleaning.

SYSTEM MONITOR ALGORITHM

The following sections describe the algorithm methodologies utilized in connection with the monitoring functions.

Active Flow "Timebase"

The various system monitoring functions (e.g. column missing, flow rate, trityl efficiency, bottle empty) require the detector data to execute. Also required are the valve opening and closing events which correlate with the detector signal. The system records both types of data with respect to a specialized "timebase". The monitor task operates in parallel with the synthesis task to carry out the above functions while synthesis takes place.

The active flow timebase is established by a clock which runs only while fluids are flowing. The clock starts when any valve opens and stops when all valves close. Detector data are taken only while this clock is running. The times of valve openings and closings are marked in terms of time on this clock.

This timebase may be understood by recognition that the only elapsed time which matters to the monitor task is time which elapses while liquids are flowing. This is true because: 1) detector readings taken while flow is stopped remain static because nothing is changing in the detector optical path; 2) after a valve event, the detector sees the effect only after fluid has flowed through the volume of tubing between the valve and the detector.

Monitor Task Data Tables

The monitor task maintains several tables of data necessary to execute its monitor functions. These tables are described below.

Detector Data Buffer

A principal table maintained by the monitor task is the detector data buffer. In this buffer it records a modified version of the signal sensed by the detector 19. The modified version is obtained by subtracting the raw detector data point-by-point from 1023 and recording the differences. The effect of this conversion is to invert the "sense" of detector data so that values are high for high absorbance reagents, and low for low absorbance reagents. Data in the detector data buffer are not reagent absorbances. They are similar to absorbance data only in the sense that high absorbances correspond to high values in the detector data buffer.

The detector data buffer is empty at the start of a synthesis, and during the first six minutes of elapsed time on the active flow time clock it becomes filled with detector data taken at 20-ms intervals. Thereafter, at any given time during the synthesis it contains detector data acquired during the preceding six minutes in the active flow timebase.

Valve Command Buffer

The second principal table is the valve command buffer. This buffer contains a record of each valve opening and valve closing event during a synthesis step. the buffer is empty at the beginning of a synthesis and is emptied again at the end of each step.

The information recorded for each valve event is: 1) the identity of the valve, 2) whether the valve opened or closed, and 3) the time of the event in the active flow timebase.

Trityl Efficiency Buffer

A third table is the trityl efficiency buffer. This buffer lists the peak heights detected during each deblock step of a synthesis (see FIG. 6). The process employed to determine these peak heights is discussed below. The use of these peak heights is for measurement of trityl yields and evaluation of coupling efficiency discussed previously.

Region Buffer

A region buffer is a table of information about specific intervals of detector data which are examined to detect empty reagent bottles. Each interval is referred to as "region", and twenty such region may be defined within any step of a synthesis.

The record for each region consists of: 1) the times (in the active flow timebase) of the first valve opening and the last valve closing in the region, and 2) a list of the reagent control valves which were open at any time in the region.

Reagent Offset Table

For bottle empty detection the monitor task must know when to expect each reagent to be present at the detector. As a first approximation, each reagent is expected to appear at the detector at a fixed time interval (in the active flow timebase) after the applicable reagent control valve is first opened. Note however that the first approximation entails considerable uncertainty which will be accounted for in the manner as discussed later. The reagent offset table maintains a record of the fixed time interval for delivery of acetonitrile to detector 19, established from each bottle during initial flow rate testing when the system is installed.

Reagent Transmittance Table

For the operation of several functions the monitor task employs the reagent transmittance table. As the name implies, this table contains a record of the detector signal levels which characterize the reagents used on the synthesizer. These values are determined by averaging several signal readings for each reagent during a transmittance calibration procedure. Each record also indicates the number of readings averaged and the standard deviation of the readings.

Monitor Data Analysis Algorithms

The monitor task analyzes the above-described data to decide whether any error conditions exist. There are several features of the monitor algorithms.

Helium Spike Suppression

Small helium bubbles which appear at random times in the midst of liquid flow pass quickly through the detector and tend to affect the detector signal for forty milliseconds or less (see peaks 100 in FIG. 7). During the affected period the detector data buffer may acquire as many as three consecutive anomalous readings. Helium spike suppression removes these spurious signal readings from the detector without affecting the data for large helium bubbles.

Figure 8:
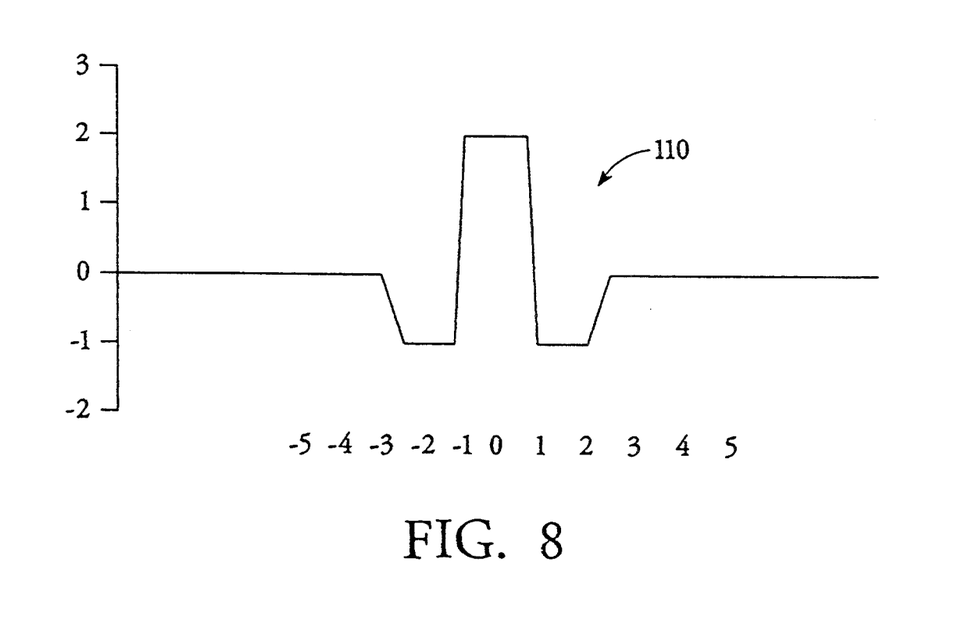
FIG. 8 is a representation of the digital filter function utilized to convolve detector data to locate helium spikes in the detector signal.
Figure 9A:
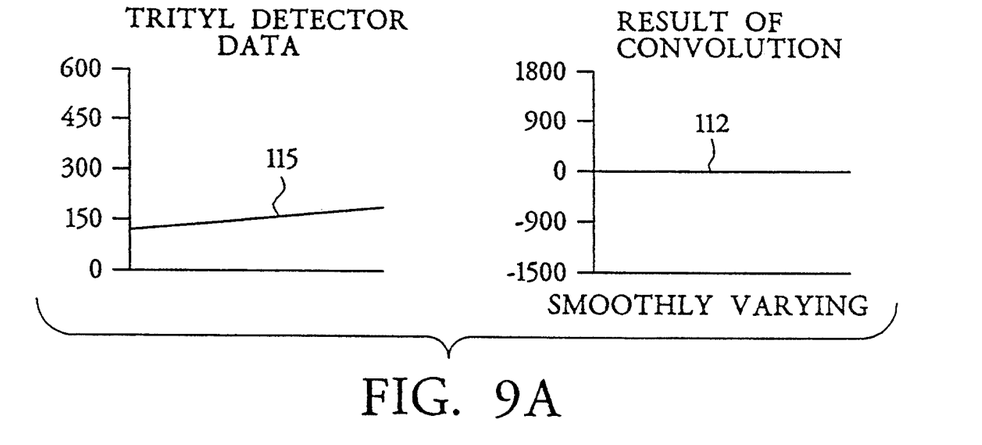
FIG. 9A–C illustrates the results of convolution using the digital filter function of FIG. 8 with different types of detector data.
Figure 9B:
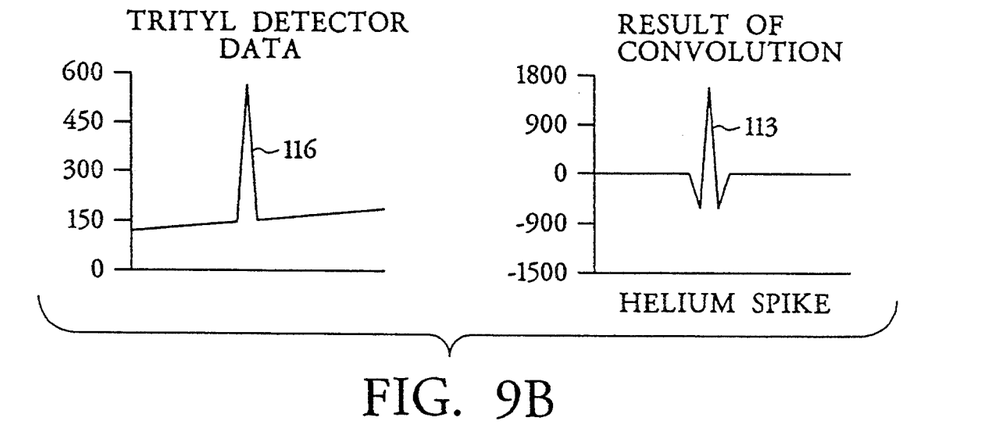
Figure 9C:
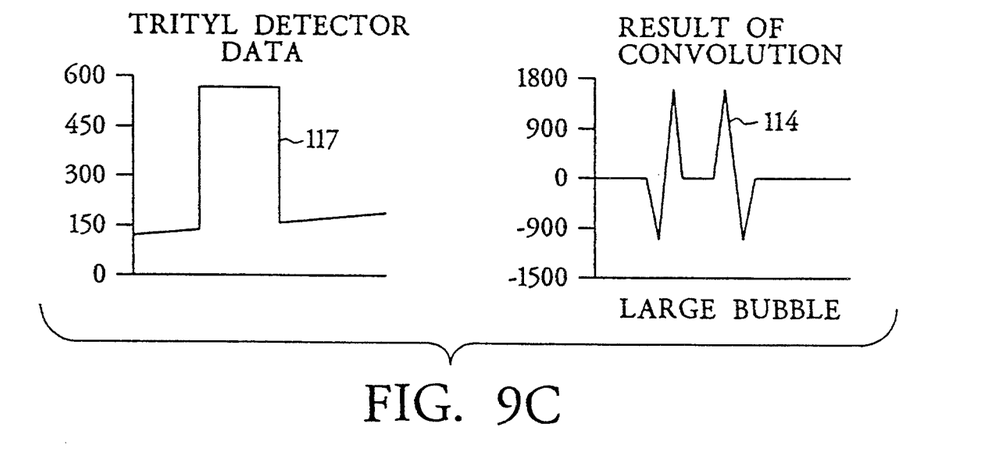

Helium spikes are located by convolving data in the detector buffer with the "1-2-1" digital filter function 110 illustrated in FIG. 8. Wherever the detector data vary smoothly with time, the result of this convolution is a function which is nearly zero everywhere. However, when the detector data contain sharp discontinuities such as a helium spike or the steep change in signal level associated with the leading or trailing edge of a helium bubble, the result contains large non-zero values. FIGS. 9A–C illustrates the result of convolution (112, 113 and 114) with three different characteristic patterns of detector data (namely, smoothly varying 115, helium spike 116 and large helium bubble 117).

The monitor task examines the result of the convolution point-by-point. Wherever the result indicates that a helium spike exists in the detector data, it suppresses the spike by setting that data point equal to the average of several nearby data points.

Flow rate testing, flow rate calibration, reagent transmittance calibration, detector calibration and offset calibration all employ the data after helium spikes have been suppressed by the above method.

Deblock Data Filtering

In addition to the helium spike suppression described above, detector data in the deblock step are further smoothed before analysis by the trityl peak evaluation algorithm below. The second smoothing function examines each point and the four following points in the spike suppressed data. From this set of five points, it averages the three lowest points and replaces the initial point with this average.

Trityl Peak Evaluation

On any step in which deblock reagent is delivered, the monitor task finds the maximum of the spike-suppressed, filtered data. It then determines the trityl peak height by subtracting the reagent transmittance value for deblock reagent from the maximum.

Flow Rate Measurement

The measurement of flow rates has been described above. The only additional point to be mentioned here is to describe criteria by which the monitor task senses transitions from the helium signal level to the acetonitrile signal level and back again. Detection of these transitions is complicated by the fact that tiny segments of acetonitrile commonly become entrained in the helium flow. Passage of any of these acetonitrile segments through the detector must not be mistaken for a true transition.

The monitor employs values for acetonitrile and helium found in the reagent transmittance table to judge when these reagents are present. During the initial phase of the flow rate test it examines spike-suppressed data point-by-point, searching for the occurrence of the acetonitrile signal level. When it detects three such values in a row, it records the time of the first of the three points as the time of the acetonitrile transition. During the second phase of the flow rate test, the same criterion is applied in reverse to detect the transition to helium flow. In this case the monitor searches for three consecutive occurrences of the helium signal level.

Detecting Empty Bottle (Primary Test)

Empty bottles are detected by analyzing data gathered in the region buffers described above, and then by applying confirmatory tests as required. To set up the primary tests for empty bottles, the user selects (or system is programmed to select) regions of the method where empty bottles will be detectable. Generally speaking, suitable regions include delivery of the reagents in question, and do not include delivery of any helium. In particular, such regions satisfy the following criteria:

1. The region is preceded by at least 300 milliseconds of liquid flow after the last previous helium valve opening (200 milliseconds in the case of testing for acetonitrile empty).
2. The region is followed by at least 300 milliseconds of liquid flow before the next following helium valve opening (200 milliseconds in the case of testing for acetonitrile empty).
3. Reagents delivered in the region do not entrain a segment of helium which is left in the tubing such as by a "solvent blocking" procedure (discussed in connection with solvent wash and helium purge above).
4. The region is at least 450 milliseconds and less than 60 seconds long. (The ideal region length is about 850 milliseconds.)
5. Preferably, the region is located near the beginning of reagent delivery for all reagents except deblock and oxidize reagents. Preferably, it is located near the end of delivery for either deblock or oxidize reagents.

Wherever the user or system has identified a suitable detection region according to the above criteria, it designates the beginning and end of the region by inserting first and second commands to the monitor task at the beginning and end of the region, during which information is gathered and store for subsequent analysis. The monitor task responds to the first command by noting the time of the first valve opening and by storing a list of all valves which open at any time in the region. It responds to the second command by noting the time of the last valve closing in the region and by reviewing the list of valve openings to ascertain which reagents delivered in the region have the highest and the lowest values in the reagent transmittance table. It stores the highest value plus 20% of the helium transmittance value as the maximum expected transmittance value for the region. It stores the lowest value minus 20% of the helium transmittance value as the minimum expected transmittance value for the region. It further examines the list of valve openings to characterize the region as a 'deblock' region, a 'capping' region, an 'oxidize' region, a 'coupling' region or a 'wash' region. It assigns each region to one and only one of these classes, based upon the identities of the reagents being dispensed.

Data collected in response to the first and second commands are not acted upon immediately; they are held in a region buffer until completion of a sequence of operations known collectively as a "Step". At that time the monitor task reviews data in all the region buffers in the step to determine whether an empty bottle occurred in any of them.

The first task in evaluating whether an empty bottle occurred is to determine when the reagents delivered in a region were expected to pass through the detector 19. The monitor task looks up the offset time in the reagent offset table corresponding to the first valve opening event. It adjusts the tabulated time to compensate for effects of synthesis scale and for characteristics of the region type (i.e. 'deblock', 'oxidize', etc.). It then adds the adjusted reagent offset time to the first valve opening and final valve closing times to find the time interval during which the reagents should have been in the detector. This is the nominal time interval for the detection region. Then, because the reagent offset times are not exact, it adds 200 milliseconds to each end of the interval (450 milliseconds in the case of a 'wash' region) to define a time window during which all reagents delivered in the detection region were assured to have appeared in the detector 19. This is the empty bottle detection window for the detection region.

Finally, the monitor task examines detector readings collected during the empty bottle detection window:

1. It counts the number of detector readings whose values are characteristic of the reagents delivered in the region; these are the 'good' readings. To find the 'good' readings the monitor evaluates data smoothed by the helium spike suppression algorithm described previously.
2. It counts the number of readings whose values are characteristic of helium; these are the 'helium' readings. To find 'helium' readings the monitor evaluates unsmoothed data directly from the detector data buffer.

3. If the number of 'good' readings is less than a particular threshold, or if the number of 'helium' readings is greater than another threshold, the monitor task concludes that there is a probable empty bottle in the region.

For all region types except 'deblock' and 'oxidize', detector readings are counted as 'good' if they lie between the minimum and maximum expected transmittance values for the region. For all region types except 'oxidize' readings are counted as 'helium' if they lie in the range from 80% to 120% of the average helium value in the reagent transmittance table. For 'oxidize' regions, they are counted if they lie in the range from 80% to 115%. For 'deblock' and 'oxidize' regions, different criteria are applied to count 'good' readings: any reading which is less than 90% or greater than 110% of the average helium value in the reagent transmittance table is counted as 'good'. Furthermore, e.g. for "deblock" and "oxidize" regions the monitor task may not count readings throughout the entire empty bottle detection window. The monitor starts examining smoothed detector data at the center of the window, and counts readings toward both ends. If it encounters a non-'good' reading in either direction it skips five readings in that direction and resumes counting. If a second non-'good' reading is encountered before reaching the end of the window, it stops counting in that direction. The same procedure is applied in the opposite direction.

As stated above, the totals of 'good' readings and 'helium' readings are compared with applicable thresholds to judge whether a probable empty bottle exists. These empirically determined thresholds are related to the region type, to the scale of synthesis and to the total number of readings taken during the nominal time interval.

Detect Empty Bottles (Confirmatory Test)

If the monitor task concludes by any of the above criteria that a probable empty bottle exists, then it immediately applies a second test to confirm the primary test. For the confirmatory test, the monitor task delivers additional quantities of the probable empty reagent and either acetonitrile or helium.

For all reagents except oxidizer, the monitor delivers several seconds of acetonitrile followed by 85 to 250 milliseconds of the suspect reagent (amount depends on synthesis scale and on which reagent), followed by several seconds more of acetonitrile. If the bottle is indeed empty, the reagent valve opening introduces helium into the stream of acetonitrile. The monitor task calculates an expected arrival time in the detector and examines unsmoothed detector data in the vicinity of the expected arrival time to count the number of 'helium' readings. If the count exceeds a scale-dependent threshold, it confirms the conclusion that the bottle is empty. In the event that an empty bottle is confirmed, the monitor repeats the confirmatory test once.

For oxidize reagent, a similar test is applied, except that the oxidize reagent delivery is sandwiched between two helium deliveries. The monitor counts the number of detector readings higher than a threshold which is 115% of the average helium value or 90% of the average oxidize reagent value in the reagent transmittance table (whichever is lower). The test confirms that the oxidize reagent bottle is empty if too few readings exceed the threshold. In the event that an empty bottle is confirmed, it repeats this test.

After completion of the confirmatory test the system washes the flow path with acetonitrile and helium. If an empty bottle condition is detected and twice confirmed, it pauses synthesis.

In addition to the primary empty bottle test described above, the monitor task also declares a probable empty bottle whenever the quantity of reagent in the bottle is calculated to be within three standard deviations of empty. (The system is programmed to keep tack of estimates of reagent usage for processes following replenishment of a reagent bottle.) In this instance, it applies confirmatory tests at the end of the step just as if the condition had been detected by the primary empty bottle test.

SYSTEM CONTROL PROGRAMMING

For the various system functions described above, the software programming of the controller 30 requires ordinary programming skills given the enabling disclosure of the desired functions to be accomplished. Hence, discussion of software programming is omitted herein.

While the invention has been described with respect to the illustrated embodiment in accordance therewith, it will be apparent to those skilled in the art that various modifications and improvements may be made without departing from the scope and spirit of the invention. Accordingly, it is to be understood that the invention is not to be limited by the specific illustrated embodiment, but only by the scope of the appended claims.

We claim:

1. An automated chemical reaction processing apparatus comprising:

a plurality of reservoirs containing reagents for use in a desired chemical reaction process;

a reaction chamber in fluid communication with the reagent reservoirs;

means for controlling delivery of said reagents in a predetermined sequence to the reaction chamber with the reagents passing through the reaction chamber defining an effluent;

means for introducing a bubble of gas into the effluent to determine a flow rate of the effluent throughout the system;

means, located downstream of the reaction chamber, for monitoring characteristics of the effluent from the reaction chamber by transmitting incident radiation through the effluent, said monitoring means including a means for detecting radiation exiting the effluent, the detecting means transducing the radiation into electrical signals, processing means connected to receive said signals and discriminate between deviations in the radiation exiting the effluent with respect to the incident radiation, whereby the processing means receives a signal from the detecting means representing the bubble.

2. The apparatus as in claim 1 wherein the reagents are of the type suitable for use in a nucleic acid synthesis process and the controlling means regulates delivery of the reagents in accordance with such nucleic acid synthesis process.

3. The apparatus as in claim 1 wherein the means for detecting is positioned along a flow path of the effluent from the reaction chamber.

4. The apparatus as in claim 3 wherein the means for monitoring senses at a single location along a flow path of the effluent.

5. The apparatus as in claim 1 wherein the processing means is programmed to determine variations in two or more of the following system conditions: reaction efficiency, reagent depletion, flow rate and flow blockage.

6. The apparatus as in claim 1 wherein the introducing means injects the bubble at a known time whereby the processing means determines whether there is blockage in the flow by failing to receive a signal, representing the bubble, from the detector.

7. The apparatus as in claim 1 wherein the introducing means controls delivery of at least one of the reagents from at least one of the reservoirs at a known time whereby the processing means determines whether there is depletion of said at least one reagent in said at least one reservoir by referencing the expected effect of said reagent passing by the monitoring means.

8. The apparatus as in claim 1 wherein said introducing means injects said bubble to create a liquid gas interface, whereby the monitoring means detects the presence of said interface.

9. The apparatus as in claim 8 wherein the monitoring means further includes means for checking flow rate from a distance traveled by the interface and elapsed time before detection.

10. An automated nucleic acid synthesis apparatus comprising:
- a plurality of reagent reservoirs containing reagents suitable for use in nucleic acid synthesis;
- a reaction chamber having a solid support suitable for nucleic acid synthesis reaction, said reaction chamber in fluid communication with the reagent reservoirs;
- means for controlling delivery of said reagents to the reaction chamber in a predetermined sequence suitable for nucleic acid synthesis with the reagents being delivered to the reaction chamber defining an effluent;
- means for introducing a bubble of gas into the effluent to determine a rate of continuous flow throughout the apparatus;
- means for monitoring characteristics of an effluent from the reaction chamber by transmitting incident light through the effluent, said monitoring means including a means for detecting light exiting said effluent, said detecting means transducing said exiting light into electrical signals; and
- processing means connected to receive the signals and discriminate between deviations between the incident radiation and the radiation exiting the effluent, the deviations representing measured characteristics of the effluent, whereby the processing means compares measured characteristics with the expected characteristics and determines the flow rate by receiving a signal from the detecting means representing the bubble, both the measured and the expected characteristics including absorbance and reflectance.

11. The apparatus as in claim 10 wherein the detecting means is positioned along a flow path of the effluent.

12. The apparatus as in claim 10 wherein the processing means is programmed to determine variations in two or more of the following system conditions: reaction efficiency, reagent depletion, flow rate and flow blockage.

13. The apparatus as in claim 11 wherein the processing means includes means for halting synthesis operation when the synthesis efficiency is determined to be below a predetermined level.

14. The apparatus as in claim 10 wherein the monitoring means includes a blue LED source and the detecting means is along a flow path of the effluent for sensing LED source.

15. The apparatus as in claim 14 wherein the blue LED source is aligned with respect to the flow path at a single location along the flow path from the reaction chamber.

16. The apparatus as in claim 14 wherein the processing means includes means for halting synthesis operation when a difference between the synthesis efficiencies of two synthesis cycles is greater than a predetermined value.

17. The apparatus as in claim 10 wherein the monitoring means comprises active flow timebase means for keeping track of timing delivery of reagents, whereby the processing means utilizes timing information from the active flow timebase means to correlate monitored effluent characteristics and expected effluent characteristics with respect to time.

* * * * *